(12) United States Patent
Shiino et al.

(10) Patent No.: US 11,540,645 B2
(45) Date of Patent: Jan. 3, 2023

(54) CONTROL DEVICE AND ELECTRIC FURNITURE

(71) Applicant: Paramount Bed Co., Ltd., Tokyo (JP)

(72) Inventors: Toshihide Shiino, Tokyo (JP);
Shinnosuke Kubota, Tokyo (JP);
Tadahiko Sakamaki, Tokyo (JP);
Shunsuke Yokoo, Tokyo (JP)

(73) Assignee: PARAMOUNT BED CO., LTD, Tokyo (JP)

( * ) Notice: Subject to any disclaimer, the term of this patent is extended or adjusted under 35 U.S.C. 154(b) by 313 days.

(21) Appl. No.: 16/637,962

(22) PCT Filed: Nov. 30, 2018

(86) PCT No.: PCT/JP2018/044147
§ 371 (c)(1),
(2) Date: Feb. 10, 2020

(87) PCT Pub. No.: WO2019/176186
PCT Pub. Date: Sep. 19, 2019

(65) Prior Publication Data
US 2020/0178702 A1    Jun. 11, 2020

(30) Foreign Application Priority Data

Mar. 12, 2018    (JP) .............................. JP2018-044696

(51) Int. Cl.
*A47C 31/00*    (2006.01)
*A47C 21/00*    (2006.01)
(Continued)

(52) U.S. Cl.
CPC .......... *A47C 31/008* (2013.01); *A47C 21/003* (2013.01); *A61B 5/0245* (2013.01);
(Continued)

(58) Field of Classification Search
CPC ... A47C 31/008; A47C 21/003; A61B 5/0245; A61B 5/11; G05B 15/02; G06F 3/015
(Continued)

(56) References Cited

U.S. PATENT DOCUMENTS 10,194,753 B2 * 2/2019 Fleury .................. A47C 31/008
2010/0101022 A1   4/2010 Riley et al.
(Continued)

FOREIGN PATENT DOCUMENTS

CN          1335679 A     2/2002
CN        202598764 U    12/2012
(Continued)

OTHER PUBLICATIONS

International Search Report PCT/ISA/210 for International Application No. PCT/JP2018/044147 dated Feb. 26, 2019.
(Continued)

*Primary Examiner* — Kerri L McNally
(74) *Attorney, Agent, or Firm* — Harness, Dickey & Pierce, PLC (57) ABSTRACT

According to one embodiment, a control device includes a user interface device. The user interface device includes an operation receiver that is capable of receiving a command operation for a movable part of the electric furniture. At least one of a brightness and a color of at least a portion of the user interface device changes on the basis of a fluctuation of a first signal. The first signal corresponds to a biological signal that includes at least one of the respiration and the heartbeat of the user of the electric furniture.

18 Claims, 8 Drawing Sheets

(51) Int. Cl.
  *G05B 15/02* (2006.01)
  *A61B 5/0245* (2006.01)
  *A61B 5/11* (2006.01)
  *G06F 3/01* (2006.01)

(52) U.S. Cl.
  CPC ............... *A61B 5/11* (2013.01); *G05B 15/02* (2013.01); *G06F 3/015* (2013.01)

(58) Field of Classification Search
  USPC .......................................................... 340/500
  See application file for complete search history.

(56) References Cited

U.S. PATENT DOCUMENTS

| | | | | |
|---|---|---|---|---|
| 2014/0094224 | A1* | 4/2014 | Lozovoy | G06F 1/3212 455/566 |
| 2015/0164721 | A1* | 6/2015 | Miyashita | G06V 40/161 5/617 |
| 2016/0022218 | A1* | 1/2016 | Hayes | A61B 5/7275 600/595 |
| 2018/0184984 | A1* | 7/2018 | Zerhusen | A61B 5/7445 |

FOREIGN PATENT DOCUMENTS

| | | |
|---|---|---|
| CN | 104582661 A | 4/2015 |
| CN | 204316780 U | 5/2015 |
| EP | 1180352 A1 | 2/2002 |
| JP | 2001-095858 A | 4/2001 |
| JP | 2004-125784 A | 4/2004 |
| JP | 2008-140156 A | 6/2008 |
| JP | 2010-201001 A | 9/2010 |
| JP | 5483579 B2 | 5/2014 |
| JP | 2016-27897 A | 2/2016 |

OTHER PUBLICATIONS

Written Opinion PCT/ISA/237 for International Application No. PCT/JP2018/044147 dated Feb. 26, 2019.

"Learning Manual of PSG Chart; Polysonogram, Sleep Stage Scoring, Interpretation", Sleep Computing Committee (Japanese Society of Sleep Research, http://issr.ip/oshirase/association/psg_data/PSGchartJ.pdf) Apr. 1, 2018.

Rechtschaffen A. et al., "A Manual of Standardized Terminology, Techniques and Scoring System for Sleep Stages of Human Subjects", BIS/BRI University of California, Los Angeles, pp. 1-2 and appendix, 1968.

"Proposed supplements and amendments to 'A Manual of Standardized Terminology, Techniques and Scoring System for Sleep Stages of Human Subjects', the Rechtschaffen & Kales (1968) standard," Psychiatry and Clinical Neurosciences, vol. 55 pp. 305-310, 2001.

* cited by examiner

CONTROL DEVICE AND ELECTRIC FURNITURE

TECHNICAL FIELD

The embodiments of the present disclosure relate to a control device and an electric furniture.

BACKGROUND ART

There are, for example, electric articles of furniture in which the height, angle of the back rest, and the like can be changed (for example, electric beds, electric chairs, and the like). These electric articles of furniture are operated by a hand-held switch or similar control device (for example, a remote controller). There is a demand for improved ease of use for such remote controllers.

CITATION LIST

Patent Literature

Patent Literature 1: Japanese Patent No. 5483579

SUMMARY OF INVENTION

Technical Problem

The embodiments of the present disclosure provide a control device and an electric furniture whereby the ease of use can be improved.

Solutions to Problem

According to one embodiment, a control device includes a user interface device. The user interface device includes an operation receiver that is capable of receiving a control operation of a movable part of an electric furniture. At least one of a brightness and a color of at least a portion of the user interface device changes on the basis of a fluctuation of a first signal. The first signal corresponds to a biological signal that includes at least one of respiration and a heartbeat of a user of the electric furniture.

According to another embodiment, a control device includes a user interface device. The user interface device includes an operation receiver that is capable of receiving a command operation for a movable part of the electric furniture. At least one of a brightness and a color of at least a portion of the user interface device changes on the basis of a first signal. The first signal corresponds to a biological signal that includes a body movement of a user of the electric furniture.

Advantageous Effects of the Invention

The embodiments of the present disclosure provide a control device and an electric furniture whereby the ease of use can be improved.

BRIEF DESCRIPTION OF THE DRAWINGS (a) and (b) of FIG. 1 are schematic perspective views illustrating a control device and an electric furniture according to Embodiment 1.

(a) to (d) of FIG. 2 are graphs illustrating operations of the control device according to Embodiment 1.

(a) and (b) of FIG. 6 are schematic drawings illustrating the electric furniture according to Embodiment 1.

(a) and (b) of FIG. 7 are schematic plan views illustrating a control device according to Embodiment 2.

DESCRIPTION OF EMBODIMENTS

Hereinafter, embodiments of the present disclosure are described while referencing the drawings.

The drawings are schematic or conceptual drawings, and the relationships between the thicknesses and the widths of the various components, the size ratios among the components, and the like may differ from the actual components. Even when the same components are illustrated, depending on the drawing, the dimensions and ratios may be illustrated differently.

In the present description and the various drawings, elements that are identical to those described for a previous drawing are marked with the same reference numerals, and detailed descriptions thereof are appropriately forgone.

Embodiment 1

Figure 1:
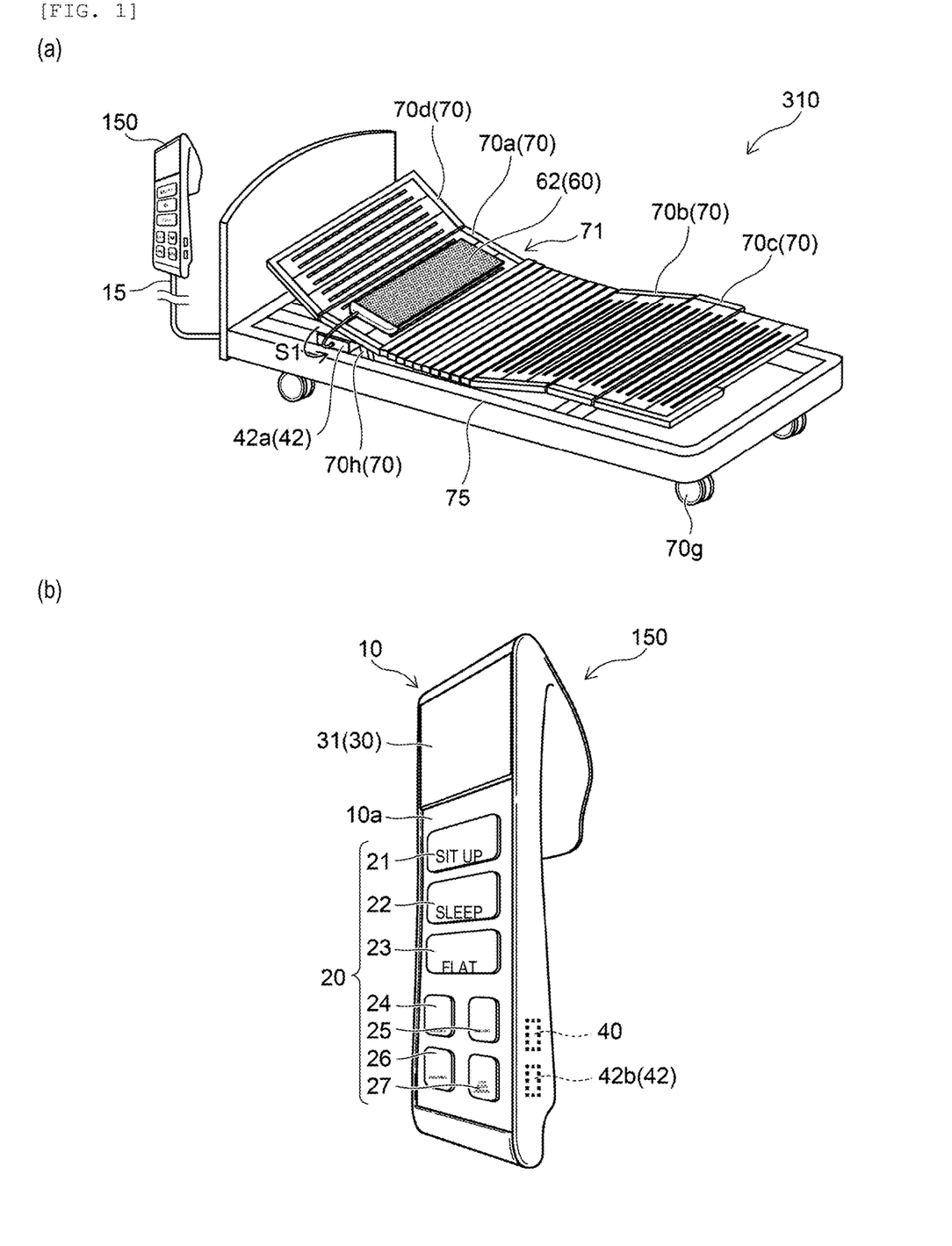

FIG. 1 (a) and FIG. 1 (b) are schematic perspective views illustrating a control device and an electric furniture according to Embodiment 1.

As illustrated in FIG. 1 (a), a control device 150 according to Embodiment 1 is used together with an electric furniture 310. The control device 150 can control movable parts 70 of the electric furniture 310. In one example, the control device 150 is implemented as a remote controller of the electric furniture 310. For example, the control device 150 is a hand-held switch. The control device 150 may have various functions such as a function of turning a light ON and OFF, a function of calling a nurse or a caregiver, and a function of turning power ON and OFF.

In one example, the electric furniture 310 is used in a household or the like. The electric furniture 310 may also be used in, for example, a lodging facility, a hospital, a nursing home, or the like.

In this example, the electric furniture 310 is an electric bed. The electric bed includes movable parts 70. The movable parts 70 include a section 71. A mattress, for example, is placed on the section 71 (not illustrated in FIG. 1). A user of the electric bed lays down on the mattress.

In one example, the movable parts 70 include a back section 70a, an upper leg section 70b, a lower leg section 70c, a height changer 70h, and the like. The height changer 70h is, for example, a bed lifter. As in the example illustrated in FIG. 1, the movable parts 70 may further include a head section 70d. Angles among the plurality of constituents included in the section 71 (the back section 70a, the upper leg section 70b, the lower leg section 70c, and the head section 70d) are changeable.

For example, the angle of the back of the user can be changed by operating the back section 70a. The angle of the knees can be changed by operating the upper leg section 70b and the lower leg section 70c. The angle of the head (or the height of the head) of the user can be changed by operating the head section 70*d*. These angles may be changed in conjunction with each other. Note that these angles are relative to a frame 75 of the bed. In one example, the frame 75 is set substantially parallel to the floor. In this case, the angle of the section 71 may be an angle that is relative to the floor. In this example, casters 70*g* are provided on the bottom of the frame 75. Note that the casters 70*g* may be omitted and replaced with "legs."

In one example, the height changer 70*h* can change the distance (height) between the floor and the bed surface. A configuration is possible in which the height changer 70*h* is capable of independently changing the height of the head side of the bed and the height of the foot side of the bed. As a result, the overall incline of the bed surface can be changed.

It is possible to perform at least any of "raise back", "raise knees", "adjust height", and "recline" by operating the movable parts 70. Here, "recline" may include rolling and/or tilting.

In one example, the control device 150 is electrically connected to the movable parts 70. However, a configuration is possible in which a control circuit is provided between the control device 150 and the movable parts 70. Thus, the state of being electrically connected also includes cases in which other circuits are interposed. In this example, a first controller 42*a* is provided between the control device 150 and the movable parts 70. The first controller 42*a* is capable of controlling the movable parts 70. In the example illustrated in FIG. 1 (*a*), the first controller 42*a* is provided under the section 71. However, the first controller 42*a* may be provided at any location.

In one example, the control device 150 is connected to the electric furniture 310 via a cable 15. However, a configuration is possible in which the control device 150 is connected to the electric furniture 310 via wireless communication.

As illustrated in FIG. 1 (*b*), the control device 150 includes a user interface device 10. The user interface device 10 includes a first surface 10*a*. In one example, the first surface 10*a* is an operation surface.

The user interface device 10 includes an operation receiver 20. The operation receiver 20 is provided on the first surface 10*a*. The operation receiver 20 can receive command operations for the movable parts 70 of the electric furniture 310. In one example, an operator of the control device 150 performs the command operations. The operator is, for example, a user of the electric furniture 310 or the like. Alternatively, a nurse or a caregiver of the user may operate the user interface device 10 (the control device 150).

In one example, the operation receiver 20 is implemented as a plurality of operation buttons. For example, pressing a "Sit up" button 21 raises the angle of the back section 70*a*. Pressing a "Sleep" button 22 adjusts the angle of the back section 70*a* to a preset angle. Pressing a "Flat" button 23 sets the angle of the section 71 to zero degrees. Pressing a "Swelling" button 24 raises the angles of the upper leg section 70*b* and the lower leg section 70*c*. Pressing a "Lower back pain" button 25 adjusts the angle of the back section 70*a*, the angle of the upper leg section 70*b*, and the angle of the lower leg section 70*c* so as to relieve the burden on the lower back of the user. Pressing a "Breathing" button 26 raises the angle of the head section 70*d*. Pressing a "Low blood pressure" button 27 adjusts the angle of the back section 70*a* to a preset angle. Here, the angle of the back section 70*a* is set to less than 12 degrees, for example. These changes are performed by operating the movable parts 70. In one example, the operations described above are performed while the respective operation buttons are pressed and held. As a result, safe operations can be realized.

The operation receiver 20 may be implemented as any type of input device, such as switches that include mechanical connections, capacitive input devices, optical input devices, or the like (for example, touch switches, a touch panel, or the like).

As illustrated in FIG. 1 (*b*), a display unit 30 may be provided on the first surface 10*a*. In one example, the display unit 30 includes a first display 31. The first display 31 is capable of displaying, for example, information about the movable parts 70 of the electric furniture 310 (the angles, the heights, and the like of the sections). The first display 31 may also display information about the functions and/or the operating state of the operation receiver 20.

In this embodiment, a detection unit 60 is provided (see (a) of FIG. 1). The detection unit 60 detects a biological signal of the user of the electric furniture 310. The biological signal includes, for example, at least one of the respiration and the heartbeat of the user. In this example, the detection unit 60 is placed on the section 71 (for example, the back section 70*a*). For example, the detection unit 60 is provided between the section 71 and a mattress.

In this embodiment, at least one of the brightness and the color of at least a portion of the user interface device 10 changes in accordance with on the biological signal of the user. In one example, the detection unit 60 described above detects the biological signal.

In one example, the detection unit 60 outputs a first signal S1 corresponding to the biological signal. The first signal S1 is sent to the first controller 42*a*, for example. The sending is carried out via the cable 15, for example. Note that the sending may be carried out via a wire or wirelessly.

In one example, the biological signal changes in accordance with the state of the user. In the embodiments, the biological signal includes at least one of the respiratory rate and the heart rate of the user. The respiratory rate is defined as the number of breaths per unit time. The heart rate is defined as the number of heartbeats per unit time. The unit time is, for example, one minute. These biological signals are related to the state of a human (the user).

Furthermore, the biological signal fluctuates with time in accordance with the state of the human. For example, when awake, the biological signal (the respiratory rate and/or the heart rate) is more likely to fluctuate in accordance with the activity of the human. However, when asleep, the fluctuation of the biological signal (the respiratory rate and/or the heart rate) is smaller than when awake.

Even while the user is asleep, the biological signal changes in accordance with the state of sleep. For example, humans experience REM sleep and Non-REM sleep while asleep. During REM sleep, low amplitude brainwaves similar to those when awake are generated. Moreover, REM sleep is accompanied with rapid eye movement. During Non-REM sleep, spindle waves or high-amplitude delta waves occur in electroencephalograms. "A manual of standardized terminology, techniques and scoring system for sleep stages of human subjects", Rechtschaffen A, KalesA eds, BIS/BRI University of California, Los Angeles, 1968 and "Learning Manual of PSG Chart; Polysonogram, Sleep Stage Scoring, Interpretation", Sleep Computing Committee (Japanese Society of Sleep Research, http://jssr.jp/oshirase/association/psg_data/PSGchartJ.pdf) include definitions of REM sleep and Non-REM sleep that can be used. These two non-patent documents are incorporated in their entirety by reference. Additionally, by using sleep polygraphy (PSG), it is possible to confirm awake and sleeping states such as the REM stage and the Non-REM stages (for example, sleep stages 1 to 4). For example, the fluctuation of the biological signal during REM sleep is larger than the fluctuation of the biological signal during Non-REM sleep.

In one example, the fluctuation of the first signal S1 is derived. In this embodiment, at least one of the brightness and the color of at least a portion of the user interface device 10 changes on the basis of the fluctuation of the first signal S1 that corresponds to the biological signal.

Specifically, the state of at least a portion of the user interface device 10 (the control device 150) changes in accordance with the state of the user. For example, when the user is sleeping, the user interface device 10 is dark. When the user is awake, the user interface device 10 is bright. When the user transitions from deep sleep to light sleep, the user interface device 10 becomes brighter. When the user is in deep sleep, the user interface device 10 is dark. As a result of such control, the user can use the user interface device 10 (the control device 150) with less discomfort. According to this embodiment, a control device and an electric furniture can be provided whereby the ease of use can be improved.

For example, with smartphones and the like, there is a technique in which the screen turns on when the user is holding the smartphone and the screen turns off when the smartphone is not held for a certain period of time. In this case, the smartphone includes an accelerometer that detects acceleration (force) applied to the smartphone and controls the screen of the smartphone in accordance with the detection results. This type of technique is carried out to suppress consumption of the battery of the smartphone.

In contrast, in this embodiment, the user interface device 10 is controlled on the basis of the biological signal of the user. For example, the awake state or the sleeping state (including deep sleep or light sleep) of the user can be estimated from the biological signal. Obstruction of the sleep of the user can be suppressed due to the state of the user interface device 10, which is used to control the bed or the like, being controlled in accordance with the state of the user. Moreover, the user can use the user interface device 10 more easily due to the user interface device 10 being placed in an appropriate state (for example, an appropriate brightness) when the user wakes up due to a difficulty staying asleep. As a result, the quality of sleep of the user can be improved. Additionally, greater convenience of operation can be provided.

In this embodiment, for example, at least one of the brightness and the color of at least a portion of the display unit 30 (the first display 31 or the like) changes on the basis of the fluctuation of the first signal S1. For example, a configuration is possible in which at least one of the brightness and the color of at least a portion of a plurality of operation receivers 20 (for example, operation buttons) changes on the basis of the fluctuation of the first signal S1.

The fluctuation of the first signal S1 includes, for example, at least one of a change over time of the first signal S1 and a change in the amplitude of the first signal S1. For example, the fluctuation when the period between the minimum value and the maximum value of the first signal S1 is short is larger than the fluctuation when the period between the minimum value and the maximum value of the first signal S1 is long. For example, the fluctuation when the difference between the minimum value and the maximum value of the first signal S1 is large is larger than the fluctuation when the difference between the minimum value and the maximum value of the first signal S1 is small.

In one example, the control unit 42 controls the state of the user interface device 10, which is based on the first signal S1 that corresponds to the biological signal and the force applied to the user interface device 10. In this example, the control unit 42 includes the first controller 42a that is provided on the electric furniture 310 (see FIG. 1 (a)), and a second controller 42b that is provided on the user interface device 10 (see FIG. 1 (b)).

As described above, in this embodiment, the state (the brightness, the color, or the like) of the user interface device 10 changes on the basis of the biological signal. In this embodiment, a configuration is possible in which the state of the user interface device 10 changes on the basis of a force (or vibration or the like) that is applied to the user interface device 10. In one example, a force (vibration or the like) is applied to the user interface device 10 when the operator holds the user interface device 10. At such a time, the user interface device 10 may become brighter. In one example, as illustrated in FIG. 1 (b), the user interface device 10 includes a user interface device sensor 40. The user interface device sensor 40 detects the force (or vibration) or the like that is applied to the user interface device 10. The state (the brightness, the color, or the like) of the user interface device 10 may change on the basis of the detection results of the user interface device sensor 40.

Hereinafter, examples of changes in the state (the brightness and the color) of the user interface device 10 are described.

Figure 2:
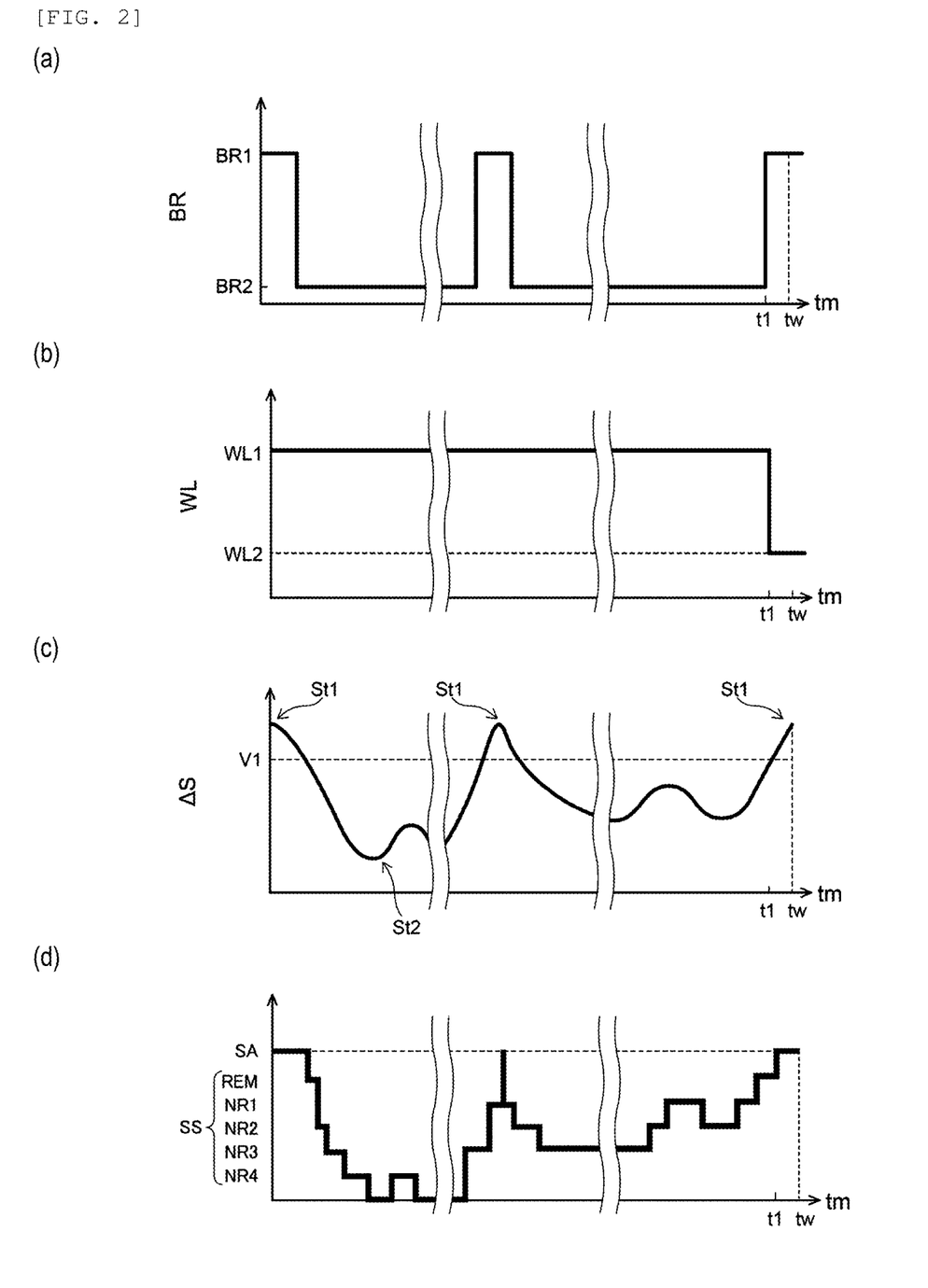

FIG. 2 (a) to FIG. 2 (d) are graphs illustrating operations of the control device according to Embodiment 1.

Time tm is represented on the horizontal axes of these graphs. The brightness BR of the at least a portion of the user interface device 10 is represented on the vertical axis of FIG. 2 (a). The peak wavelength WL (for example, the color) of the at least a portion of the user interface device 10 is represented on the vertical axis of FIG. 2 (b). The fluctuation ΔS of the first signal S1 is represented on the vertical axis of FIG. 2(c). The sleep stages and awake state of the user of the electric furniture 310 are represented on the vertical axis of FIG. 2(d).

As illustrated in FIG. 2(c), the fluctuation ΔS of the first signal S1 changes with the time tm. For example, prior to the user falling asleep (the left edge of FIG. 2(c)), the fluctuation ΔS is great. Upon the user falling asleep, the fluctuation ΔS lessens. For example, a state in which the fluctuation ΔS is greater than a first value V1 (threshold value) is defined as a first state st1. A state in which the fluctuation ΔS is less than or equal to the first value V1 is defined as a second state st2. The first state st1 is an awake state or an awakening state. The second state st2 is a sleeping state. In another example, the first state st1 may be a REM sleep state, and the second state st2 may be a Non-REM sleep state.

The fluctuation ΔS of the first signal S1 changes in accordance with the sleeping state of the user. For example, the fluctuation ΔS is thought to be larger when the user is sleeping lightly (for example, when in REM sleep) than when the user is sleeping deeply (for example, when in NREM sleep). The sleeping and awake states of the user and also the depth of sleep of the user can be estimated from the fluctuation ΔS of FIG. 2(c). For example, international criteria allows for classification based on the following:

Alpha waves and low-amplitude fast waves occur in the awake state SA.

Alpha waves are less than 50% and low-amplitude brain waves, humps, slow eye movements, and the like occur at stage NR1 of the sleeping state SS.

Spindle waves, K complexes, humps, and the like occur at stage NR2.

Slow waves (delta waves) occur at stages NR3 and NR4.

The REM sleep stage REM is the same as stage NR1 in that rapid eye movement and the like occur, but there are no humps.

As illustrated in FIG. 2(d), the state of the user changes between the awake state SA and the sleeping state SS. The sleeping state SS can, for example, be divided into the REM sleep stage REM and the Non-REM sleep stages (for example, stages NR1 to NR4). For example, sleep is light at the REM sleep stage REM, and sleep is deep at stage NR4.

In this embodiment, as illustrated in FIG. 2 (a) and FIG. 2(b), the brightness BR of the at least a portion of the user interface device 10 changes on the basis of the fluctuation ΔS. The brightness BR is a first brightness BR1 when in the first state st1 (for example, when the user is in the awake state SA or in REM sleep) where the fluctuation ΔS exceeds the threshold value (the first value V1). The brightness BR is a second brightness BR2 when in the second state st2 (for example, when the user is in Non-REM sleep) where the fluctuation ΔS is less than or equal to the threshold value (the first value V1). The second brightness BR2 is darker than the first brightness BR1. The second brightness BR2 may be an OFF state.

The user interface device 10 may execute a first operation and a second operation. In the first operation, the brightness of the at least a portion of the user interface device 10 is raised when the fluctuation ΔS increases. The fluctuation ΔS increases when, for example, the user enters the awake state SA from the sleeping state SS, or when the sleep of the user lightens. At this time, the brightness of the at least a portion of the user interface device 10 is increased by the first operation. For example, the at least a portion of the user interface device 10 is changed from the second brightness BR2 to the first brightness BR1.

In the second operation, the brightness of the at least a portion of the user interface device 10 is lowered when the fluctuation ΔS decreases. The fluctuation ΔS decreases when, for example, the user enters the sleeping state SS from the awake state SA, or when the sleep of the user deepens. At this time, the brightness of the at least a portion of the user interface device 10 is decreased by the second operation. For example, the at least a portion of the user interface device 10 is changed from the first brightness BR1 to the second brightness BR2.

In one example, the at least a portion of the user interface device 10 becomes brighter when the user is awake or lightly asleep before (for example, in the middle of the night) a scheduled wake-up time (time tw). As a result, the user can more easily use the control device 150, for example. For example, the surroundings of the user become brighter and stumbling and falling of the user can be suppressed. Meanwhile, the at least a portion of the user interface device 10 becomes brighter and ease of operation is improved when the user is awake. Additionally, when falling asleep, the at least a portion of the user interface device 10 is darkened, and obstructions to falling asleep can be suppressed. When waking up, the brightness of the at least a portion of the user interface device 10 can be increased. As a result, the user can wake up in a pleasant manner, for example.

In this embodiment, a configuration is possible in which, as illustrated in FIG. 2(b), the peak wavelength WL of the at least a portion of the user interface device 10 changes on the basis of the fluctuation ΔS. A first time t1 is defined as a time closest to the time tw and prior to the predetermined time tw, at which the fluctuation ΔS becomes the first state st1. The color (the peak wavelength WL) may differ from before to after the first time t1. For example, the color (the peak wavelength WL) may change from a first peak wavelength WL1 to a second peak wavelength WL2. In one example, the second peak wavelength WL2 is shorter than the first peak wavelength WL1. For example, the color may change from a warm color to a cool color. When waking up, for example, the color of the at least a portion of the user interface device 10 can be changed to a blue-white color. As a result, pleasant waking up of the user can be promoted.

According to this embodiment, a control device and an electric furniture can be provided whereby the ease of use can be improved.

In this embodiment, a configuration is possible in which the user interface device 10 executes third to fifth operations in addition to the first operation and the second operation described above. The third operation and the fourth operation are performed on the basis of body movements of the user. The fifth operation is performed on the basis of time.

In the third operation and the fourth operation, the brightness of the at least a portion of the user interface device 10 is changed on the basis of a second signal that corresponds to a body movement of the user. Examples of the body movement include sitting-up, preparing to get out of bed (sitting on the edge of the bed, for example), getting out of bed, and the like. In one example, the detection unit 60 described above (see FIG. 1(a)) can detect the body movement of the user.

In the third operation, the brightness of the at least a portion of the user interface device 10 is raised when the second signal that corresponds to the body movement increases. For example, the at least a portion of the user interface device 10 becomes brighter when the user wakes up or gets out of bed.

In the fourth operation, the brightness of the at least a portion of the user interface device 10 is lowered when the second signal that corresponds to the body movement decreases. For example, the at least a portion of the user interface device 10 is darkened when the movement of the user becomes smaller.

In the fifth operation, the brightness of the at least a portion of the user interface device 10 is lowered when a predetermined amount of time has elapsed without an operation being input into the operation receiver 20. For example, the at least a portion of the user interface device 10 is darkened when the user ceases to operate the control device 150.

In this embodiment, the brightness and the color of the at least a portion of the user interface device 10 are, for example, controlled by the control unit 42. In this example, the control unit 42 includes the first controller 42a and the second controller 42b. Any wired or wireless configuration can be used for the sending and receiving of information (signals) between the control unit 42 and the control device 150 and the sending and receiving of information (signals) between the control unit 42 and the electric furniture 310.

Hereinafter, some examples of configurations and operations of the control device are described.

Figure 3:
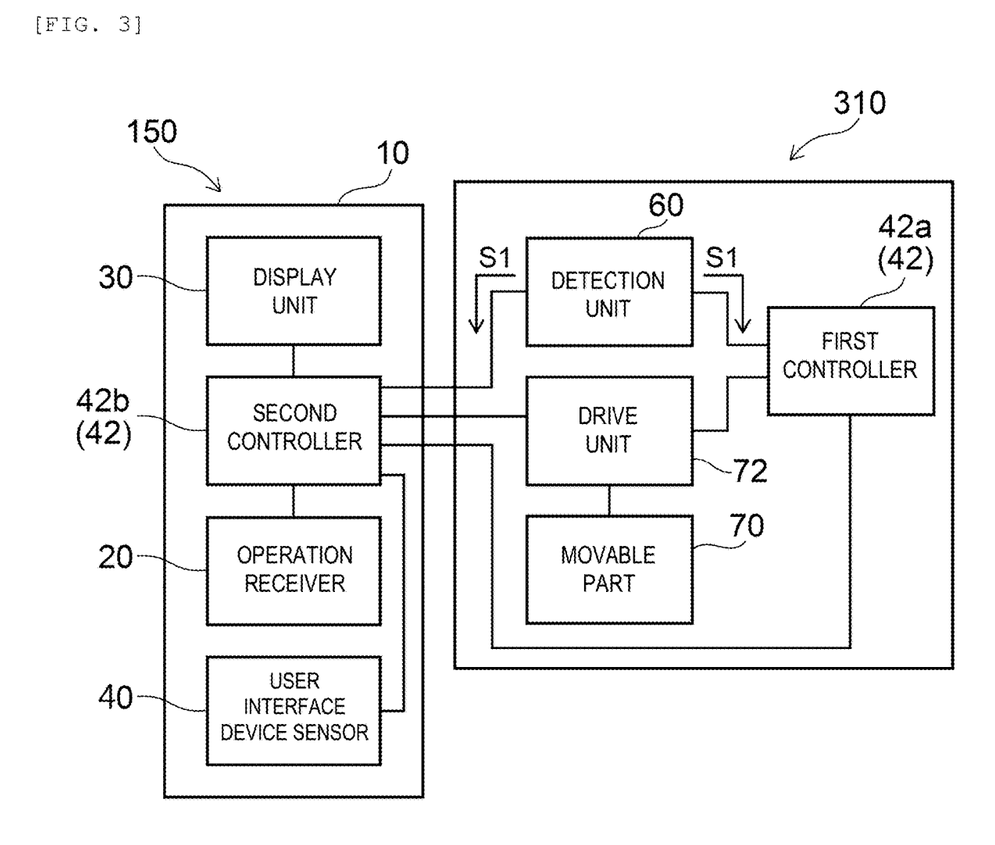
FIG. 3 is a block diagram illustrating the control device and the electric furniture according to Embodiment 1.

FIG. 3 is a block diagram illustrating the control device 150 and the electric furniture 310 according to Embodiment 1. As illustrated in FIG. 3, the control device 150 includes the operation receiver 20, the display unit 30, the user interface device sensor 40, and the control unit 42.

The display unit 30 is provided on the first surface 10a, for example. The user interface device sensor 40 and the control unit 42 are provided in space inside the user interface device 10, for example. However, the user interface device sensor 40 and the control unit 42 may be provided at any location of the user interface device 10. In this example, the control unit 42 includes the first controller 42a and the second controller 42b. Moreover, in this example, the first controller 42a is provided on the electric furniture 310. However, the first controller 42a may be provided on a tablet terminal, for example. The second controller 42b is provided on the user interface device 10.

In one example, the user interface device sensor 40 includes an acceleration sensor, a vibration sensor, a pressure sensor, and/or a touch sensor. The user interface device sensor 40 may also include a temperature sensor, an illuminance sensor, an image sensor, and/or a ranging sensor.

In one example, the first controller 42a is connected to the second controller 42b, the detection unit 60, and a drive unit 72. In this example, the first controller 42a is connected via a wire. However, the first controller 42a may be connected wirelessly. In one example, the detection results from the detection unit 60 are sent to the first controller 42a. The second controller 42b is, for example, connected to the operation receiver 20, the display unit 30, the user interface device sensor 40, the first controller 42a, and the detection unit 60. For example, a signal based on a control operation received by the operation receiver 20 (for example, the buttons 21 to 27) is sent to the second controller 42b. Meanwhile, the detection results from the user interface device sensor 40 are sent to the second controller 42b. Note that the detection results from the detection unit 60 may be sent to the second controller 42b. In one example, the determination results from the first controller 42a are sent to the second controller 42b.

The display unit 30 changes the display in accordance with control signals from the second controller 42b. At least one of the brightness and the color of the display unit 30 may be changed in accordance with the control signals from the second controller 42b. Additionally, at least one of the brightness and the color of the operation receiver 20 may be changed in accordance with the control signals from the second controller 42b.

In one example, the second controller 42b is electrically connected to the electric furniture 310 via the cable 15 (see FIG. 1(a) and the like) or the like. The second controller 42b sends control signals, which correspond to control commands received by the operation receiver 20, to the electric furniture 310.

The electric furniture 310 includes the drive unit 72 in addition to the movable parts 70. The drive unit 72 is connected to the movable parts 70, and is also connected to the second controller 42b. The drive unit 72 drives the movable parts 70 in accordance with the control signals sent from the second controller 42b. As a result, the movable parts 70 move according to the control operations received by the operation receiver 20. For example, "raise back", "raise knees", "adjust height", or the like is performed. A configuration is possible in which the drive unit 72 drives the movable parts 70 according to control signals supplied from the first controller 42a. The drive unit 72 is implemented as, for example, an actuator or the like.

In one example, the drive unit 72 may include a load sensor (for example, a load cell or the like). The biological signal of the user of the electric furniture 310 may be detected by a load applied to the load sensor (the drive unit 72). This case corresponds to a configuration in which the detection unit 60 is provided in the drive unit 72 that drives the movable parts 70. Thus, the drive unit 72 may include the detection unit 60.

Hereinafter, examples of controlling the brightness and the color of the at least a portion of the user interface device 10 are described. In one example, the control unit 42 performs at least one of the various determinations described below. In this example, the first controller 42a performs various determinations. The second controller 42b changes the brightness and the color of the at least a portion of the user interface device 10 on the basis of commands from the first controller 42a.

Figure 4:
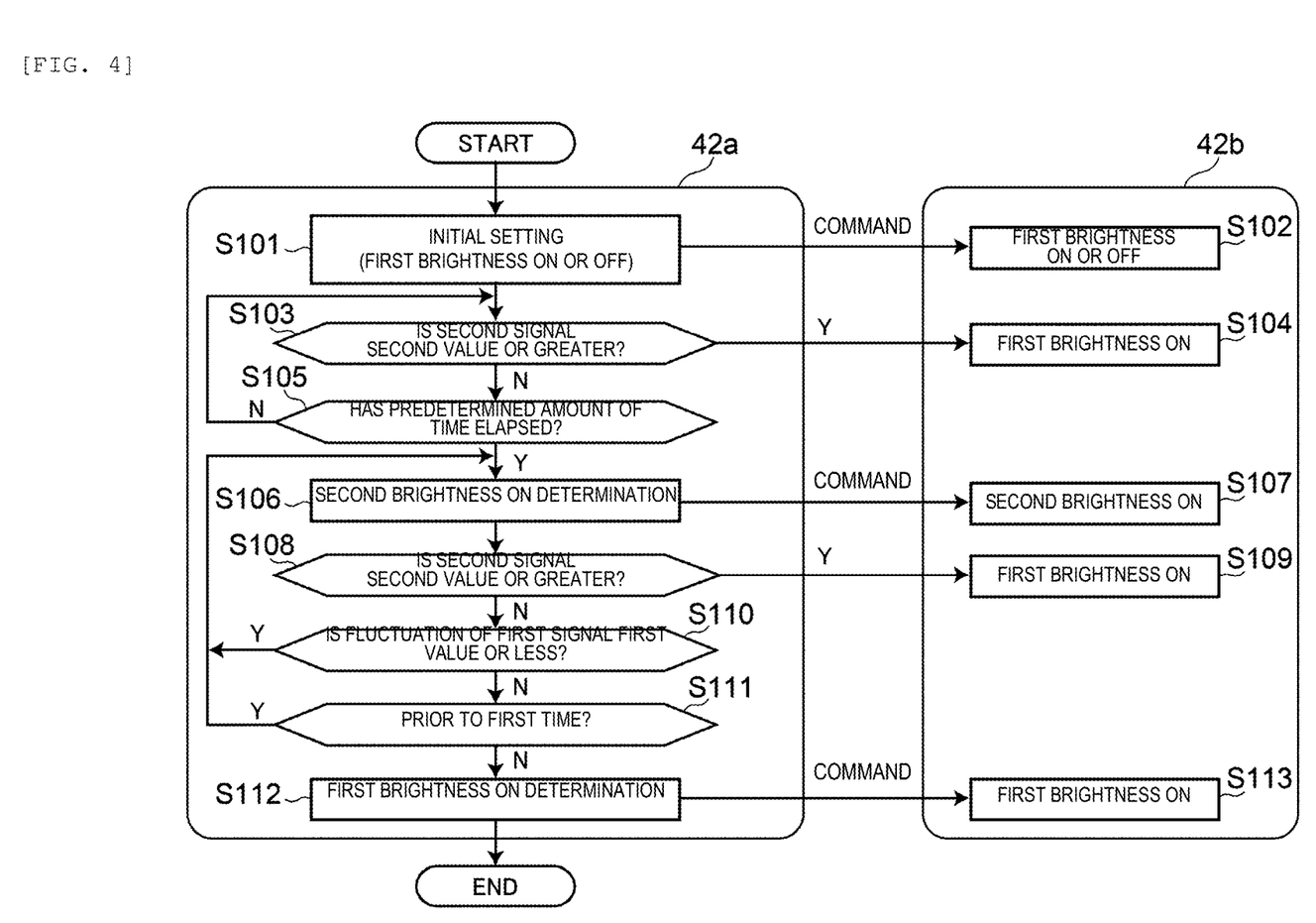
FIG. 4 is a flowchart illustrating an operation of the control device according to Embodiment 1.

FIG. 4 is a flowchart illustrating an operation of the control device 150 according to Embodiment 1.

The initial setting (the first brightness BR1 or OFF) for the brightness of the at least a portion of the user interface device 10 is determined, and the first controller 42a issues a command to the second controller 42b (step S101). The second controller 42b sets the brightness of the at least a portion of the user interface device 10 to the first brightness BR1 or the OFF state on the basis of the command from the first controller 42a (step S102).

The first controller 42a determines whether the second signal is greater than or equal to a second value. When the second signal is greater than or equal to the second value, the first controller 42a issues a command to the second controller 42b to set the brightness of the at least a portion of the user interface device 10 to the first brightness BR1 (step S103). The second controller 42b sets the brightness of the at least a portion of the user interface device 10 to the first brightness BR1 on the basis of the command from the first controller 42a (step S104).

When the second signal is not greater than or equal to the second value, it is determined whether a predetermined amount of time has elapsed without an operation being input into the operation receiver 20 (step S105). When the predetermined amount of time has not elapsed, step S103 is executed.

When the predetermined amount of time has elapsed, the first controller 42a determines to set the brightness of the at least a portion of the user interface device 10 to the second brightness BR2. The first controller 42a issues a command to the second controller 42b to set the brightness of the at least a portion of the user interface device 10 to the second brightness BR2 (step S106). The second controller 42b sets the brightness of the at least a portion of the user interface device 10 to the second brightness BR2 on the basis of the command from the first controller 42a (step S107).

The first controller 42a determines whether the second signal is greater than or equal to the second value. When the second signal is greater than or equal to the second value, the first controller 42a issues a command to the second controller 42b to set the brightness of the at least a portion of the user interface device 10 to the first brightness BR1 (step S108). The second controller 42b sets the brightness of the at least a portion of the user interface device 10 to the first brightness BR1 on the basis of the command from the first controller 42a (step S109).

When the second signal is not greater than or equal to the second value, the first controller 42a determines whether the fluctuation ΔS of the first signal S1 is less than or equal to the first value V1 (step S110). When the fluctuation ΔS is less than or equal to the first value V1, step S106 is executed.

When the fluctuation ΔS exceeds the first value V1, the first controller 42a determines whether the time is prior to the first time t1 (step S111). When the time is prior to the first time t1, step S106 is executed.

When the time is after the first time t1, the first controller 42a determines to set the brightness of the at least a portion of the user interface device 10 to the first brightness BR1. The first controller 42a issues a command to the second controller 42b to set the brightness of the at least a portion of the user interface device 10 to the first brightness BR1 (step S112). The second controller 42b sets the brightness of the at least a portion of the user interface device 10 to the first brightness BR1 on the basis of the command from the first controller 42a (step S113).

Configurations are possible in which a component other than the control unit 42 performs at least one of the various determinations described above.

Figure 5:
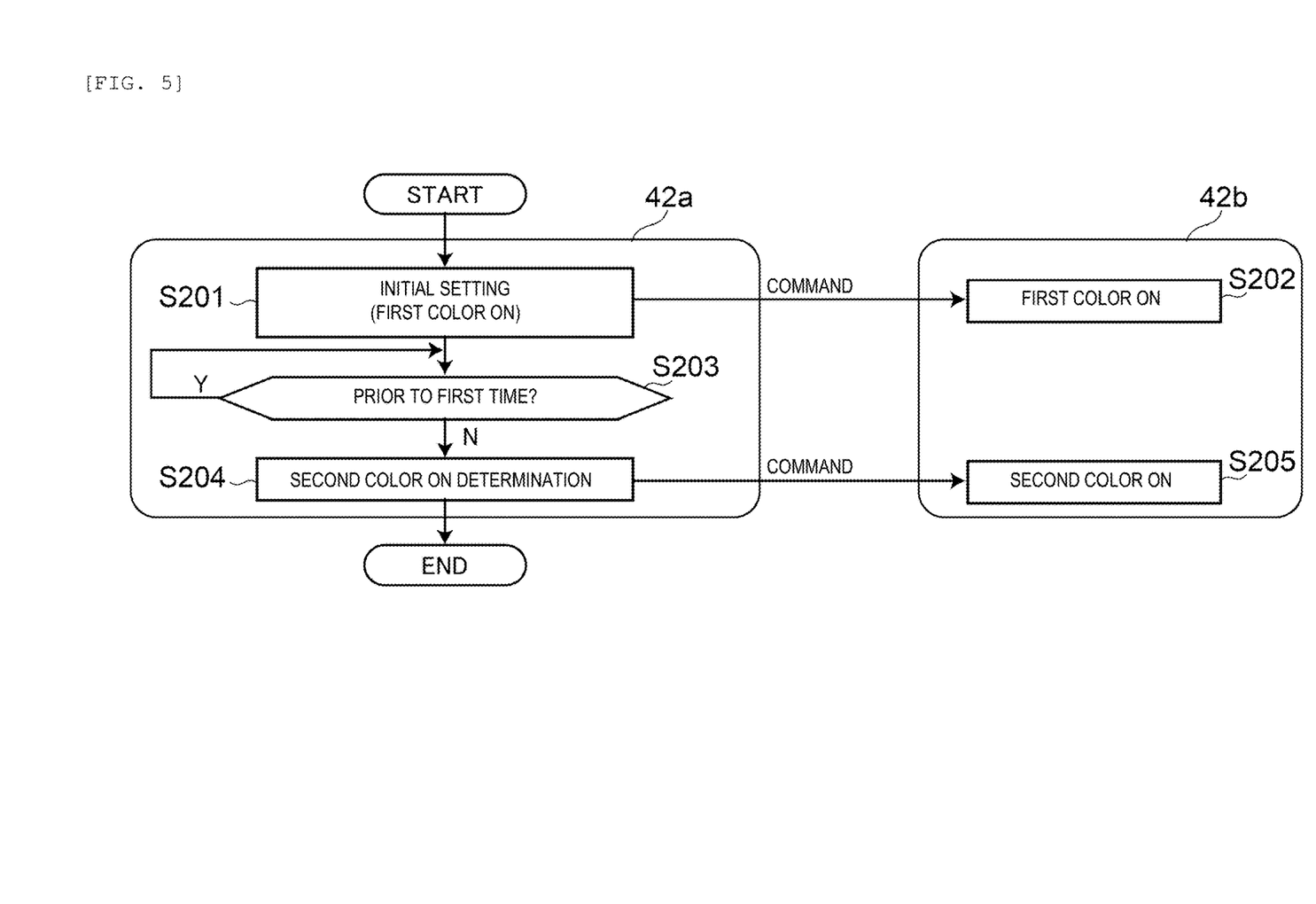
FIG. 5 is a flowchart illustrating another operation of the control device according to Embodiment 1.

FIG. 5 is a flowchart illustrating another operation of the control device 150 according to Embodiment 1.

The initial setting for the color (a first color) of the at least a portion of the user interface device 10 is determined, and the first controller 42a issues a command to the second controller 42b (step S201). The second controller 42b sets the color of the at least a portion of the user interface device 10 to the first color on the basis of the command from the first controller 42a (step S202).

The first controller 42a determines whether the time is prior to the first time t1 (step S203). When the time is prior to the first time t1, step S203 is executed. When the time is after the first time t1, the first controller 42a determines to set the color of the at least a portion of the user interface device 10 to a second color. The first controller 42a issues a command to the second controller 42b to set the color of the at least a portion of the user interface device 10 to the second color (step S204). The second controller 42b sets the color of the at least a portion of the user interface device 10 to the second color on the basis of the command from the first controller 42a (step S205). In one example, the second peak wavelength WL2 of the second color is shorter than the first peak wavelength WL1 of the first color.

Figure 6:
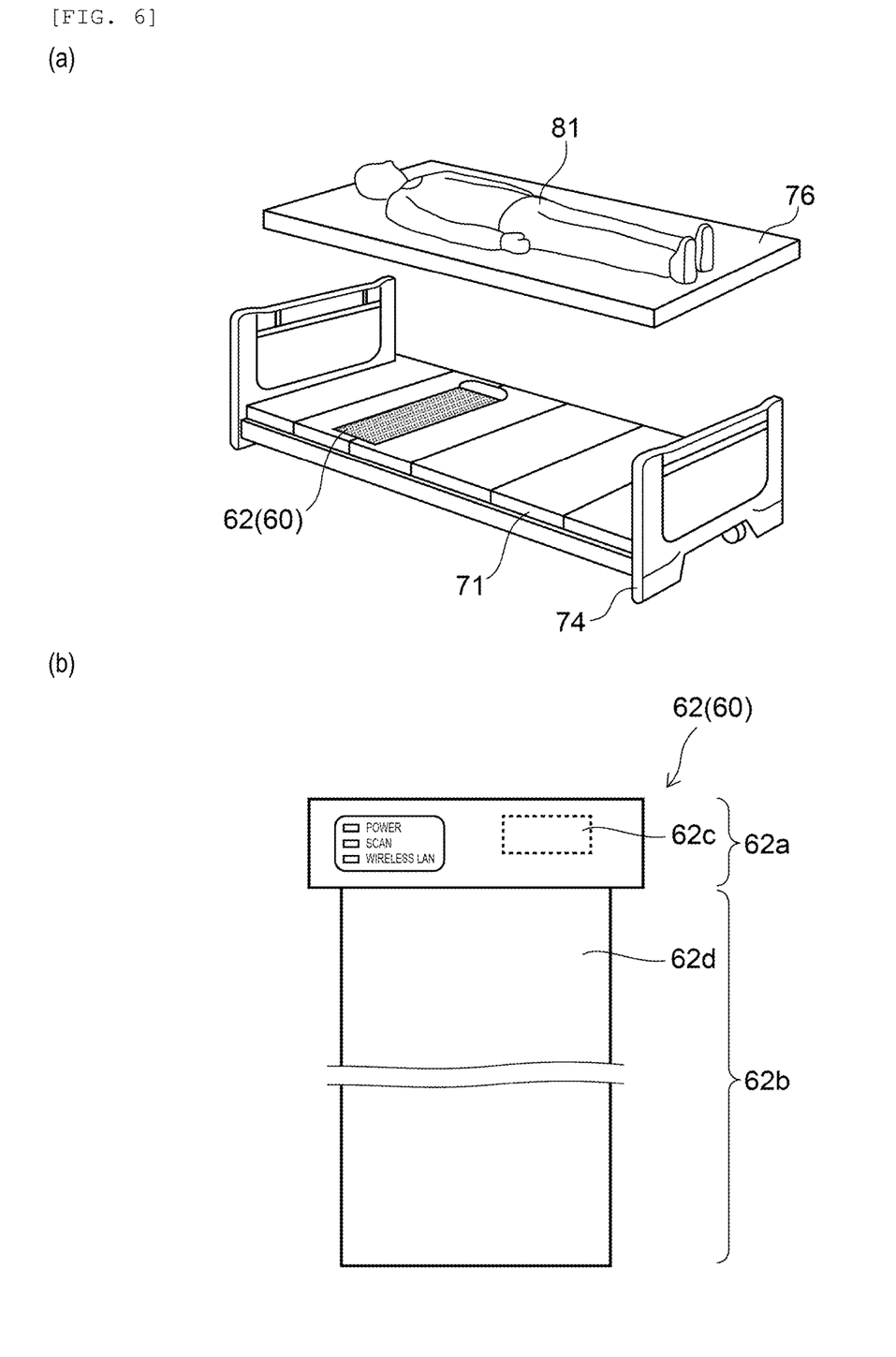

FIG. 6(a) and FIG. 6(b) are schematic drawings illustrating the electric furniture 310 according to Embodiment 1. FIG. 6(a) is a schematic perspective view illustrating the placement of a sensor 62 (example of the detection unit 60). FIG. 6(b) is a schematic plan view illustrating the sensor 62. In order to make FIG. 6(a) easier to view, the components are drawn separated from each other.

As illustrated in FIG. 6(a), the section 71 is provided on bed legs 74. A mattress 76 is provided on the section 71. A user 81 is lying down on the mattress 76. The sensor 62 (the detection unit 60) is provided between the section 71 and the mattress 76. In this example, the sensor 62 is a sheet-like or plate-like sensor.

As illustrated in FIG. 6(b), the sensor 62 includes a circuit portion 62a and a sensor portion 62b. The circuit portion 62a includes a communicator 62c. The communicator 62c sends and receives data to and from the control unit 42. Note that the sending and receiving is performed via a desired method. Examples of this method include via a wire and/or wirelessly.

In one example, the sensor portion 62b includes a sensor device 62d. The sensor portion 62b detects a force (or characteristic corresponding to a force) to which the sensor portion 62b is subjected. Examples of the force include pressure and/or sound waves. In one example, the sensor portion 62b includes a pressure sensor. In another example, the sensor portion 62b includes a microphone.

Forces from the user 81 (pressure and/or sound waves) are applied to the sensor portion 62b via the mattress 76. In one example, a signal based on a force detected by the sensor portion 62b is output from the circuit portion 62a. The output signal is sent to the control unit 42. The control unit 42 estimates the state of the user 81 (out of bed, sleeping, awake, or the like) on the basis of the magnitude of the signal (the force) and/or the change over time of the magnitude of the signal (the force). A configuration is possible in which the circuit portion 62a estimates the state of the user 81 (out of bed, sleeping, awake, or the like) on the basis of the force detected by sensor portion 62b and/or the change over time of the force. The state of the user 81 may include sitting up, sitting on the edge of the bed (for example, preparing to get out of bed), being out of bed, falling asleep, sleeping, awake, and waking up.

In one example, the sensor portion 62b is subjected to a vibration that corresponds to the state of the user 81. The vibration corresponds to a body movement of the user 81, for example. The sensor portion 62b detects the vibration. The vibration may include sound.

In one example, vibration detection means (the sensor portion 62b) and a processor (at least a portion of the circuit portion 62a and/or the control unit 42) are provided. In one example, the processor includes a computer. The vibration detection means detects, for example, a vibration of a person (the user 81) sleeping on bedding. The processor includes, for example, activity amount calculation means, sleep determination value calculation means, and sleeping state determination means. The devices are divided by function. For example, the activity amount calculation means calculates, per sampling unit time, the amount of activity of the sleeping person on the basis of the vibration detected by the vibration detection means. For example, the sleep determination value calculation means calculates, as a sleep determination value, the sum of values obtained by multiplying the amount of activity at a second time (for example, the current time) and the amount of activity calculated at a third time (for example, a time prior to the current time) by a correction factor that is weighted in accordance with time. For example, the sleeping state determination means determines an awake state when the sleep determination value exceeds a predetermined threshold, and determines a sleeping state in other cases.

The detection unit 60 described above can detect the first signal that corresponds to the biological signal, which includes at least one of the respiration and the heartbeat of the user 81. The detection unit 60 described above can detect the second signal that corresponds to the body movement of the user 81.

The first signal includes, for example, at least one selected from the group consisting of a respiratory rate, a heart rate, a pulse rate, and an electrocardiogram.

In this embodiment, the at least a portion of the user interface device 10 includes, for example, at least one selected from the group consisting of a liquid crystal display, an LED, an organic EL, and a plasma display.

In this embodiment, a configuration is possible in which the stage of sleep of the user 81 is estimated using the biological signal, and the movable parts 70 are controlled in correspondence with the sleep stage. In this embodiment, the posture of the user 81 (supine position, prone position, lateral position, or the like) may be estimated. The movable parts 70 may be controlled in accordance with the results of estimating the posture of the user 81. For example, when the posture of the user 81 is estimated to be the prone position, the raise back movement is not performed even if the raise back operation is input into the user interface device 10. As a result, the safety of the user 81 is further enhanced.

Embodiment 2

In Embodiment 2, a user interface device 10 of a control device 151 includes a display unit 30 and a plurality of operation receivers 20.

FIG. 7(a) and FIG. 7(b) are schematic plan views illustrating the control device 151 according to Embodiment 2.

Figure 7:
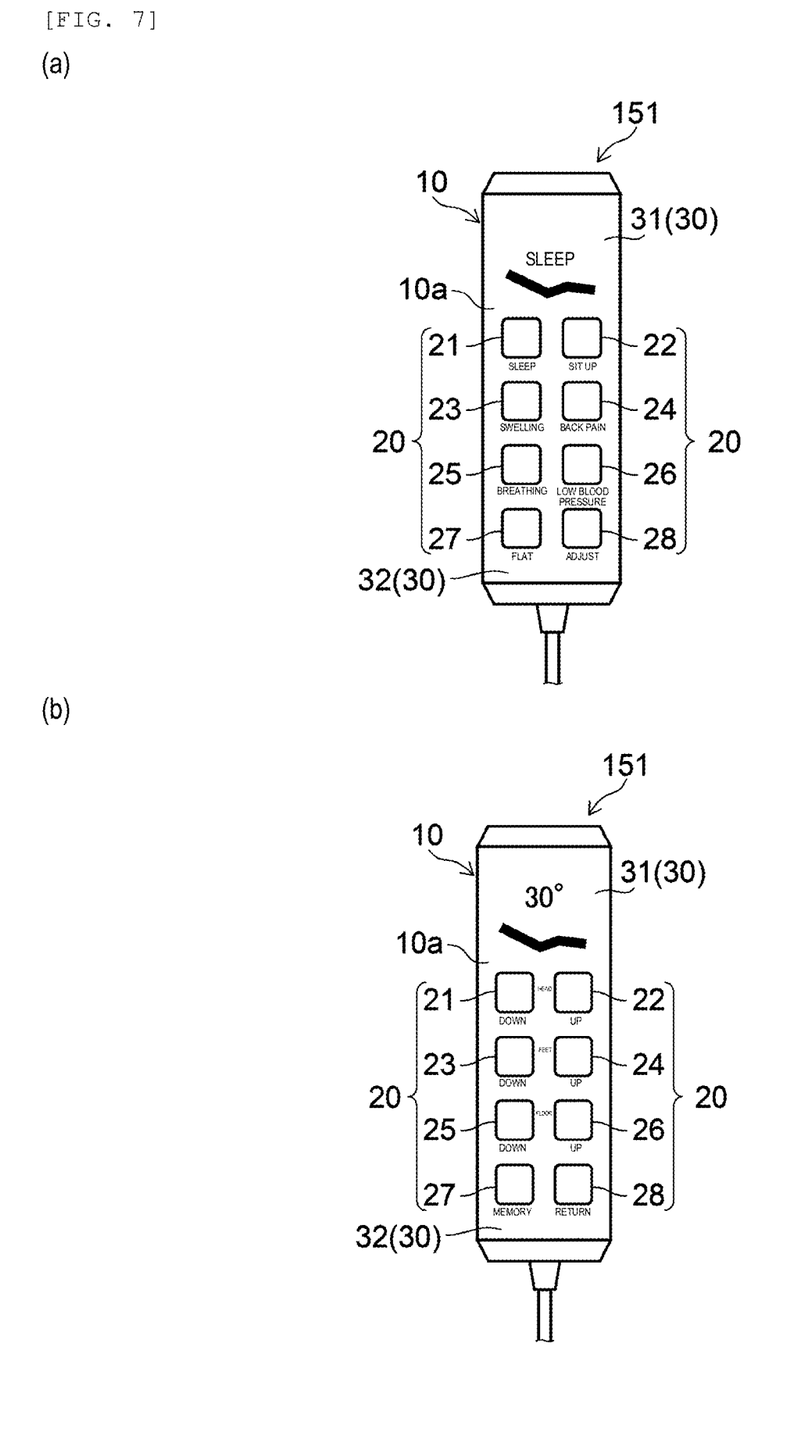

As illustrated in FIG. 7 (*a*) and FIG. 7 (*b*), the control device 151 according to the present embodiment includes the user interface device 10. The user interface device 10 includes a first surface 10*a* on which the plurality of operation receivers 20 and the display unit 30 are provided.

In the present embodiment, the plurality of operation receivers 20 are, for example, operation buttons that include mechanical connections. With such operation receivers 20, it is easier to recognize that the operation receivers 20 are being operated. For example, an elderly person can be prevented from performing unintended operations.

In the present embodiment, the display unit 30 includes a first display 31 and a second display 32. As described above, the first display 31 is capable of displaying, for example, information about the movable parts 70 of the electric furniture 310. The second display 32 is capable of displaying, for example, information about the functions and/or the operating states of the operation receivers 20. The second display 32 is provided in the vicinity of the operation receivers 20 (operation buttons, for example). For example, the second display 32 is provided in a region among the plurality of operation buttons.

In the present embodiment, the display unit 30 is implemented as a liquid crystal display. In one example, the functions of the operation buttons can be switched by changing the displayed content of the liquid crystal display. Thus, a plurality of functions can be operated without increasing the number of operation buttons. As a result, the size of the housing of the control device 151 can be reduced, for example. Additionally, the structure of the control device can be simplified, for example. The size and the color of characters that are displayed on the display unit 30 can be changed according to the user. As a result, the needs of elderly people and people with glaucoma can be accommodated.

In the present embodiment, a configuration is possible in which the plurality of operation receivers 20 provided on the first surface 10*a* are implemented as virtual buttons that are displayed on the liquid crystal display. Moreover, the plurality of operation receivers 20 and the display unit 30 may be implemented as a touch panel.

Embodiment 3

Figure 8:
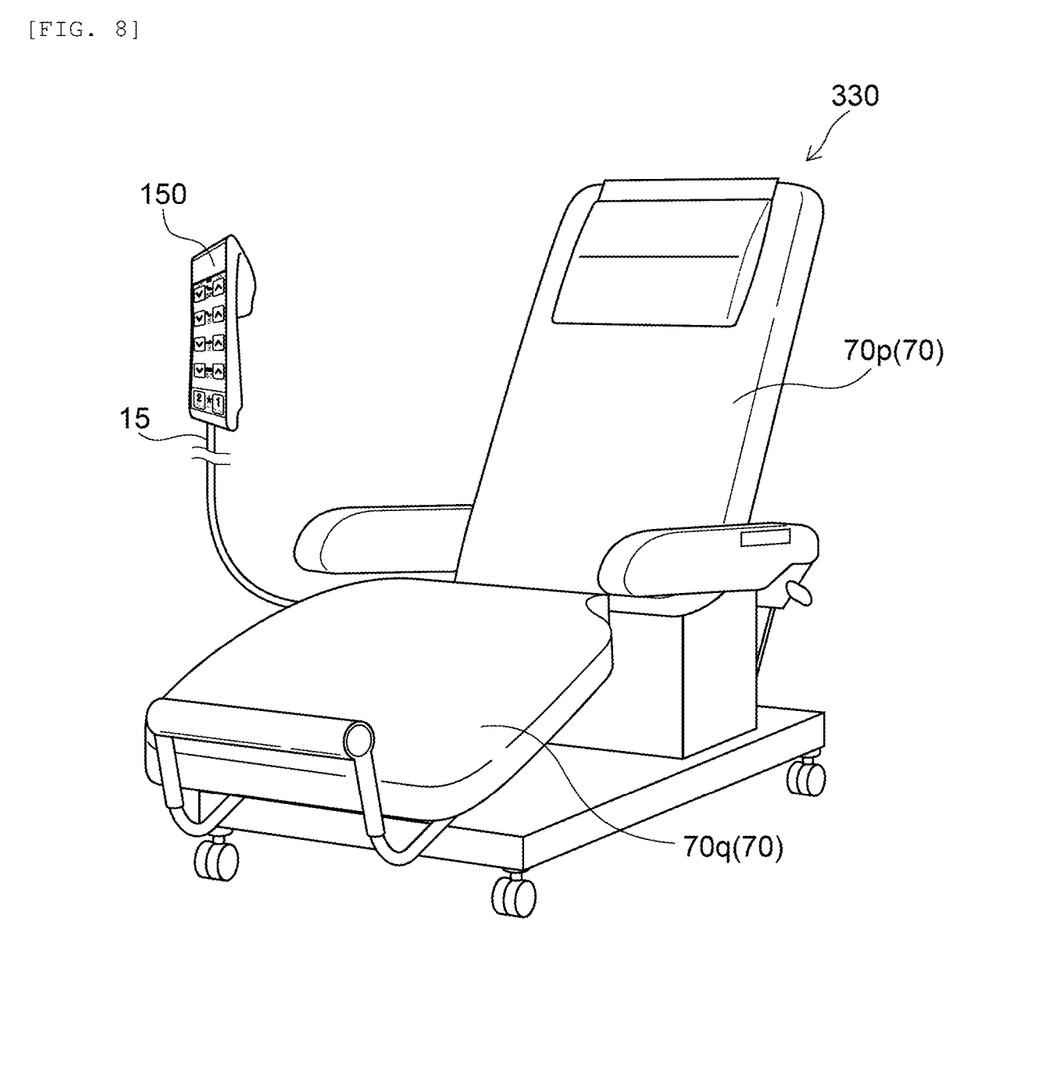
FIG. 8 is a schematic perspective view illustrating an electric furniture according to Embodiment 3.

FIG. 8 is a schematic perspective view illustrating an electric furniture 330 according to Embodiment 3.

As illustrated in FIG. 8, the electric furniture 330 is an electric chair. The electric furniture 330 includes movable parts 70. In one example, the movable parts 70 include a back rest 70*p* and a seat 70*q*. The back rest 70*p* corresponds to a section for which the angle is changeable. The seat 70*q* corresponds to the height changer. The angle of the seat 70*q* may also be changeable. These movable parts 70 are controlled by the control device 150 according to the embodiments. With the electric furniture 330 as well, the movable parts 70 move in accordance with the state of the user.

Embodiment 4

In the embodiments, a configuration is possible in which at least one of the brightness and the color of at least a portion of the user interface device 10 changes on the basis of a first signal that corresponds to a biological signal that includes a body movement of the user 81. In the present embodiment, the biological signal includes the body movement of the user 81. In one example, the body movement (number of body movements) is a number of times, per unit time, that an amplitude, greater than or equal to a predetermined value, of the waveform of a vibration obtained via the mattress continues for a predetermined amount of time or longer. However, the definition of the body movement is not limited thereto. For example, the body movement may be the number of times that an amplitude, of a vibration waveform, greater than or equal to a predetermined value continues for a predetermined amount of time or longer.

For example, when awake, the body movement is great in correspondence with the activity of the human. However, when asleep, the body movement is less than when awake. For example, the body movement during REM sleep is greater than the body movement during NREM sleep. In the present embodiment, when, for example, the first signal is large, the at least a portion of the user interface device 10 is bright (the first brightness BR1). When, for example, the first signal is small, the at least a portion of the user interface device 10 is dark (the second brightness BR2). In the present embodiment, when, for example, the first signal is greater than or equal to a predetermined value, the at least a portion of the user interface device 10 becomes brighter.

Thus, in the present embodiment, the state of the at least a portion of the user interface device 10 (the control device 150) changes in accordance with the state of the user. For example, when the user is sleeping, the user interface device 10 is dark. When the user is awake, the user interface device 10 is bright. When the user transitions from deep sleep to light sleep, the user interface device 10 becomes brighter. When the user is in deep sleep, the user interface device 10 is dark. As a result of such control, the user can use the user interface device 10 (the control device 150) with less discomfort.

The embodiments may include the following configurations (proposals):

Configuration 1

A control device including a user interface device that includes an operation receiver capable of receiving a command operation for a movable part of an electric furniture, wherein at least one of a brightness and a color of at least a portion of the user interface device changes on the basis of a fluctuation of a first signal that corresponds to a biological signal that includes at least one of respiration and a heartbeat of a user of the electric furniture.

Configuration 2

The control device according to configuration 1, wherein the at least a portion of the user interface device includes a first brightness when the fluctuation is a first state, and a second brightness when the fluctuation is a second state, the second darkness being darker than the first brightness and the second state being smaller than the first state.

Configuration 3

The control device according to configuration 1, wherein the user interface device is capable of performing a first operation of raising a brightness of the at least a portion of the user interface device when the fluctuation increases.

Configuration 4

The control device according to any one of configurations 1 to 3, wherein the user interface device is capable of performing a second operation of lowering the brightness of the at least a portion of the user interface device when the fluctuation decreases.

Configuration 5

The control device according to any one of configurations 1 to 4, wherein the user interface device is capable of performing a third operation of raising the brightness of the at least a portion of the user interface device when a second signal that corresponds to a body movement of the user increases.

Configuration 6

The control device according to any one of configurations 1 to 5, wherein the user interface device is capable of performing a fourth operation of lowering the brightness of the at least a portion of the user interface device when the second signal that corresponds to the body movement of the user decreases.

Configuration 7

The control device according to any one of configurations 1 to 6, wherein the user interface device is capable of performing a fifth operation of lowering the brightness of the at least a portion of the user interface device when a predetermined amount of time has elapsed without an operation being input into the operation receiver.

Configuration 8

The control device according to configuration 2, wherein, when the fluctuation is the first state, a color of the at least a portion of the user interface device differs from before to after a first time.

Configuration 9

The control device according to configuration 8, wherein a peak wavelength of the color of the at least a portion of the user interface device after the first time is shorter than a peak wavelength of the color of the at least a portion of the user interface device prior to the first time.

Configuration 10

A control device including a user interface device that includes an operation receiver capable of receiving a command operation for a movable part of the electric furniture, wherein at least one of a brightness and a color of at least a portion of the user interface device changes on the basis of a first signal that corresponds to a biological signal that includes a body movement of a user of the electric furniture.

Configuration 11

The control device according to any one of configurations 1 to 10, wherein the at least a portion of the user interface device includes at least one selected from the group consisting of a liquid crystal display, an LED, an organic EL, and a plasma display.

Configuration 12

The control device according to any one of configurations 1 to 11, wherein:
the user interface device further includes a display unit, and
the at least a portion of the user interface device includes at least a portion of the display unit.

Configuration 13

The control device according to any one of configurations 1 to 12, wherein the at least a portion of the user interface device includes at least a portion of the operation receiver.

Configuration 14

The control device according to configuration 13, wherein the operation receiver includes at least one of an operation button and a touch panel.

Configuration 15

An electric furniture including the control device according to any one of configurations 1 to 14.

Configuration 16

The electric furniture according to configuration 15, further including a detection unit that detects the biological signal, wherein
the control unit acquires the first signal that corresponds to the biological signal detected by the detection unit.

According to the embodiments, a control device and an electric furniture can be provided whereby the ease of use can be improved.

In the preceding, embodiments of the present invention have been described while referencing specific examples. However, the present disclosure is not limited to these specific examples. For example, one skilled in the art may similarly practice the invention by appropriately selecting specific configurations of the components included in the control device such as the user interface device, the operation receiver, the detection unit, the control unit, and the like; and such practice is included in the scope of the invention to the extent that similar effects are obtained.

Furthermore, any two or more components of the specific examples may be combined within the extent of technical feasibility and are included in the scope of the invention to the extent that the spirit of the invention is included.

Moreover, all control devices and electric furniture capable of being implemented by an appropriate design modification by one skilled in the art based on the control device and the electric furniture described above as embodiments of the invention also are within the scope of the invention to the extent that the spirit of the invention is included.

Various modifications and alterations can be conceived by those skilled in the art within the spirit of the present invention, and it is understood that such modifications and alterations are also encompassed within the scope of the invention.

DESCRIPTION OF REFERENCE NUMERALS AND SIGNS

10: User interface device, 10a: First surface, 15: Cable, 20: Operation receiver, 21 to 28: Operation buttons, 30: Display unit, 31: First display, 32: Second display, 40: User interface device sensor, 42: Control unit, 42a, 42b: First and second controllers, 60: Detection unit, 62: Sensor, 62a: Circuit portion, 62b: Sensor portion, 62c: Communicator, 62d: Sensor device, 70: Movable parts, 70a: Back section, 70b: Upper leg section, 70c: Lower leg section, 70d: Head section, 70g: Caster, 70h: Height changer, 70p: Back rest, 70q: Seat, 71: Section, 72: Drive unit, 74: Bed leg, 75: Frame, 76: Mattress, 81: User, 150, 155: Control device, 310, 330: Electric furniture, ΔS: Fluctuation, BR: Brightness, BR1, BR2: First and second brightnesses, NR1 to NR4: Stages, REM: REM sleep stage, S1: First signal, SA: Awake state, SS: Sleeping state, V1: First value, WL: Peak wavelength, WL1, WL2: First and second peak wavelengths, st1, st2: First and second states, t1: First time, tm: time, tw: time.

The invention claimed is:

1. A control device comprising:
a user interface device including
an operation receiver configured to receive a command operation for controlling an electric furniture, the electric furniture including a plurality of parts, and
a processor configured to cause the control device to,
control at least one of a brightness or a color of at least a portion of the user interface device based on a state of a user,
cause the electric furniture to move at least one of the plurality of parts in accordance with the state of the user,
cause the electric furniture to move the at least one of the plurality of parts in accordance with a posture of the user, wherein the state of the user includes at least one of
either awake or sleeping, or
a state of sleeping, and
wherein at least one part, of the plurality of parts, is configured to not move in response to the posture of the user being estimated to be a prone position.

2. The control device according to claim 1, wherein the processor is configured to cause the control device to:
change the at least a portion of the user interface device to display a first brightness in response to the state of the user being a first state; and
change the at least a portion of the user interface to display a second brightness in response to the state of the user being a second state, the second brightness being darker than the first brightness.

3. The control device according to claim 1, wherein the processor is configured to cause the control device to:
raise the brightness of the at least a portion of the user interface device in response to a fluctuation of a biological signal increasing.

4. The control device according to claim 1, wherein the processor is configured to cause the control device to:
lower the brightness of the at least a portion of the user interface device in response to a fluctuation of a biological signal decreasing.

5. The control device according to claim 1, wherein the processor is configured to cause the control device to:
raise the brightness of the at least a portion of the user interface device in response to a second signal increasing, the second signal corresponding with a body movement of the user.

6. The control device according to claim 1, wherein the processor is configured to cause the control device to:
lower the brightness of the at least a portion of the user interface device in response to a second signal decreasing, the second signal corresponding to a body movement of the user.

7. The control device according to claim 1, wherein the processor is configured to cause the control device to:
lower the brightness of the at least a portion of the user interface device in response to an amount of time elapsing without receiving an operation.

8. The control device according to claim 2, wherein the processor is configured to cause the control device to:
change the color of the at least a portion of the user interface device from a first color to a second color at a given time.

9. The control device according to claim 8, wherein a peak wavelength of the second color is shorter than a peak wavelength of the first color.

10. The control device according to claim 1, wherein the processor is configured to cause the control device to:
change at least one of the brightness or the color of at least a partial portion of the user interface device based on a biological signal, the biological signal indicating a body movement of the user.

11. The control device according to claim 1, wherein the at least a portion of the user interface device includes at least one of:
a liquid crystal display,
a light emitting diode (LED),
an organic EL, or
a plasma display.

12. The control device according to claim 1, wherein:
the user interface device further includes a display; and
the at least a portion of the user interface device includes at least a portion of the display.

13. The control device according to claim 1, wherein the at least a portion of the user interface device includes at least a portion of the operation receiver.

14. The control device according to claim 13, wherein the operation receiver includes at least one of an operation button or a touch panel.

15. An electric furniture comprising:
a plurality of parts;
and a control device including,
a user interface device including a processor configured to cause the electric furniture to
receive a command operation for controlling the electric furniture,
control at least one of a brightness or a color of at least a portion of the user interface device based on a state of a user,
move at least one of the plurality of parts in accordance with the state of the user, and
move the at least one of the plurality of parts in accordance with a posture of the user,
wherein the state of the user includes at least one of either awake or sleeping, or
a state of sleeping, and
wherein at least one part, of the plurality of parts, is configured to not move in response to the posture of the user being estimated to be a prone position.

16. The electric furniture according to claim 15, further comprising a detection unit configured to detect a biological signal, wherein
the processor is configured to cause the electric furniture to acquire a first signal related to the biological signal detected by the detection unit.

17. The control device according to claim 1, wherein the processor is configured to cause the control device to change at least one of the brightness or the color of the at least a portion of the user interface device based on a biological signal including at least one of respiration or a heartbeat of the user.

18. The control device according to claim 14, wherein the operation button includes a first function and a second function, and
the processor is configured to cause the control device to switch the first function of the operation button to the second function of the operation button.

* * * * *